(12) United States Patent
Sato et al.

(10) Patent No.: US 11,382,852 B2
(45) Date of Patent: Jul. 12, 2022

(54) ORAL COMPOSITION

(71) Applicant: GC Laboratory America Inc., Alsip, IL (US)

(72) Inventors: Takuya Sato, Alsip, IL (US); Kosuke Honda, Alsip, IL (US)

(73) Assignee: GC Laboratory America Inc., Alsip, IL (US)

( * ) Notice: Subject to any disclaimer, the term of this patent is extended or adjusted under 35 U.S.C. 154(b) by 0 days.

(21) Appl. No.: 17/038,607

(22) Filed: Sep. 30, 2020

(65) Prior Publication Data

US 2022/0096351 A1  Mar. 31, 2022

(51) Int. Cl.
*A61K 8/64* (2006.01)
*A61Q 11/00* (2006.01)
*A61K 8/362* (2006.01)
*A61K 8/21* (2006.01)

(52) U.S. Cl.
CPC .................. *A61K 8/64* (2013.01); *A61K 8/21* (2013.01); *A61K 8/362* (2013.01); *A61Q 11/00* (2013.01)

(58) Field of Classification Search
CPC ........... A61Q 11/00; A61K 8/19; A61K 8/365
USPC ............................................... 424/49, 52, 57
IPC ...................................................... A61Q 11/00
See application file for complete search history.

(56) References Cited

U.S. PATENT DOCUMENTS 3,282,792 A * 11/1966 Fiscella .................... A61K 8/21
424/52
10,278,906 B2   5/2019 Rege et al.
2016/0317404 A1 11/2016 Reynolds

* cited by examiner

*Primary Examiner* — Walter E Webb
(74) *Attorney, Agent, or Firm* — Sughrue Mion, PLLC

(57) ABSTRACT

An oral composition for treating diseases in the mouth caused by formulation of biofilms on teeth. The oral composition includes water, stannous ion source, casein phosphopeptide-amorphous calcium phosphate, and at least citric acid or a citric acid salt.

7 Claims, No Drawings

ORAL COMPOSITION

FIELD OF THE INVENTION

The present invention relates to a composition for treating diseases in the mouth caused by formulation of biofilms on teeth.

BACKGROUND ART

A biofilm is a thin, slimy layer of bacteria that adheres to surfaces, such as teeth, in the mouth. An example of a biofilm is plaque, which can lead to oral health problems such as gum disease (e.g., gingivitis and periodontitis) or cavities. Oral composition for treating such diseases are provided, for example, in the form of a mouthwash, a toothpaste, or a dental cream. The oral compositions are not swallowed, but applied to or used to treat the mouth, then expectorated.

Oral compositions for treating diseases caused by biofilms are generally known and contain stannous ion sources. Stannous ions have antibacterial activity in an aqueous solution. However, stannous ions lose antibacterial activity when the ions precipitate (e.g., in a solution where the pH has neutrality or in the presence of water). Thus, there are stability problems with stannous ions, and there is a need for an oral composition having sufficient stability of stannous ions.

To address the stability problems with stannous ions, compositions limiting the amount of water or using a chelating effect have been proposed. For example, a composition including a buffer system containing citric acid and a sodium citrate salt in an amount from 1.0% to 3.0% by weight of the composition to stabilize stannous ions in the aqueous solution has been proposed (for example, U.S. Pat. No. 10,278,906). A composition including CPP-ACP for stabilizing stannous ions has also been proposed (for example, US 2016/0317404). However, these compositions have a drawback in that the concentration of stannous ions gradually decreases as time passes. Thus, there is a need for an oral composition having sufficient stability of stannous ions after long-term storage.

SUMMARY OF THE INVENTION

An object of the present invention is to provide an oral composition having high storage stability such that the concentration of stannous ions is kept high even after long-term storage. As a result of intensive studies, the inventors discovered an oral composition having high storage such that the concentration of stannous ions is kept high even after long-term storage. In addition, the inventor also discovered that the concentration of other ions were kept high in the oral composition. The present invention was completed based on these discoveries.

An aspect of the present invention is an oral composition containing water, a stannous ion source, casein phosphopeptide-amorphous calcium phosphate (CPP-ACP), and at least citric acid or a citric acid salt. Another aspect of the present invention is a method for the treatment of diseases caused by biofilms on teeth including administering the oral composition of the present invention to the mouth.

It is to be understood that the present disclosure is not limited to the particular embodiments or examples described herein. The preferred embodiments and examples are intended for purposes of illustration only and are not intended to limit the scope of the invention.

DETAILED DESCRIPTION OF INVENTION

The present invention is explained in the following by referring to preferable embodiments thereof.

An oral composition according to the present invention contains water, a stannous ion source, CPP-ACP, and at least a citric acid or a citric acid salt. The oral composition of the present invention contains CPP-ACP and at least citric acid or the citric acid salt to prevent stannous ions from precipitating to keep the concentration of stannous ions high even after long-term storage. In addition to the concentration of stannous ions, the concentrations of fluorine ions in the oral composition of the present invention are kept high even after long-term storage. A higher concentration of fluorine ions leads to improved anti-caries activity. Further, in addition to the concentration of stannous and fluorine ions, the concentrations of calcium ions and inorganic phosphate ions in the oral composition of the present invention are kept high even after long-term storage. Higher concentrations of calcium ions and inorganic phosphate ions lead to a more improved remineralization capacity.

In an aspect of the present invention, the oral composition is a toothpaste or oral gel composition.

In an aspect of the present invention, the oral composition contains water. Preferably, the water is purified. In the oral composition of the present invention, the amount of water is preferably at least 30 mass % based on the composition. Preferably, the amount of water is at least 40 mass % based on the composition. If the amount of water is less than 30 mass %, it is difficult to dissolve the materials.

In an aspect of the present invention, the oral composition includes a stannous ion source. The stannous ion source can be a compound of stannous with counter ions, such as fluoride and chloride. Preferably, the stannous ion source is stannous fluoride. The oral composition of the present invention includes the stannous ion source in an amount of 0.2 to 0.7 mass % based on the composition. Preferably, the amount of the stannous ion source is 0.4 to 0.5 mass % based on the composition. An amount of the stannous ion is 0.15 to 0.53 mass % based on the composition, and preferably 0.3 to 0.38 mass % based on the composition.

In an aspect of the present invention, the oral composition includes a fluoride ion source. Fluoride ion sources include sodium fluoride, stannous fluoride, and sodium monofluorophosphate. Preferably, stannous fluoride is the fluoride ion source. The oral composition of the present invention includes the fluoride ion source in an amount of 0.2 to 0.7 mass % based on the composition. Preferably, the amount of the fluoride ion source is 0.4 to 0.5 mass % based on the composition. An amount of the fluoride ion is 0.05 to 0.17 mass % based on the composition, and preferably is 0.1 to 0.12 mass % based on the composition.

In a preferred embodiment of the oral composition of the present invention, the oral composition includes stannous fluoride as the stannous ion source and the fluorine ion source.

In an aspect of the present invention, the oral composition includes CPP-ACP. CPP-ACP is a calcium ion source and a phosphate ion source. The oral composition of the present invention includes CPP-ACP is an amount of 1 to 20 mass % based on the composition. If the amount of CPP-ACP is more than 20 mass % based on the composition, it is difficult for the CPP-ACP to be dissolved. Preferably, the amount of CPP-ACP is 2 to 10 mass %. More preferably, the amount of CPP-ACP is 2.5 to 10 mass % based on the composition.

In an aspect of the present invention, the oral composition includes at least citric acid or a citric acid salt. The citric acid or citric acid salt stabilizes the stannous ions in an aqueous solution by a chelating effect thereof. Examples of citric acid salt include sodium citrate, zinc citrate, and potassium citrate. In a preferred embodiment of the oral composition of the present invention, the citric acid salt is sodium citrate. The oral composition of the present invention includes at least citric acid or a citric acid salt in an amount of 2 to 8 mass % based on the composition. If the amount of citric acid or citric acid salt is above 8 mass % based on the composition, it is difficult to dissolve the materials. Preferably, the amount of citric acid or the citric acid salt is 4 to 8 mass % based on the composition.

In addition, in the oral composition of the present invention, a thickener, an abrasive, a surfactant or foaming agent, a wetting agent, a colorant, a preservative, a sweetener, or a flavor etc., can be suitably incorporated as needed in amounts which do not substantially adversely affect the properties and characteristics of the oral composition.

The oral composition may contain a thickener to improve the viscosity of the composition. Any thickener that has been conventionally used for an oral composition may be employed as the thickener. Examples of suitable thickeners include sodium carboxymethyl cellulose, sodium alginate, carboxy polymethylene, carboxymethyl cellulose, carboxymethyl cellulose sodium salt, carboxy polymethylene, calcium carboxymethylcellulose, methyl vinyl ether-maleic anhydride copolymers, sodium starch glycolate, sodium starch phosphate, sodium polyacrylate, methyl cellulose, microcrystalline cellulose, hydroxypropyl cellulose, polyvinylpyrrolidone, vinyl polymers, polysaccharide thickeners such as xanthan gum and carrageenan. Two or more may be used in combination. Preferably, the oral composition of the present invention includes sodium carboxymethyl cellulose. An example of a commercially available sodium carboxylmethyl cellulose is Cellogen F-AG. Although the amount of the thickener used is suitably adjusted according to the material to be used, the oral composition of the present invention may include the thickener in an amount of 1 mass % to 10 mass % based on the composition. Preferably, the amount of thickener is 2 mass % to 5 mass % based on the composition.

The oral composition may contain an inorganic thickener. Any thickener that has been conventionally used for an oral composition may be employed as the inorganic thickener. Examples of suitable inorganic thickeners include calcium carbonate, calcium silicate, magnesium silicate, silica powder, various glasses, amorphous hydrous silicic acid, fumed silica, and titanium dioxide. Two or more may be used in combination. Preferably, the oral composition of the present invention includes fumed silica. An example of a commercially available fumed silica is AEROSIL 200. Although the amount of the inorganic thickener used is suitably adjusted according to the material to be used, the oral composition of the present invention may include the inorganic thickener in an amount of 1 mass % to 10 mass % based on the composition. Preferably, the amount of the inorganic thickener is 2 mass % to 5 mass % based on the composition.

The oral composition of the present invention may contain an abrasive. Any abrasive that has been conventionally used for an oral composition may be employed as the abrasive. Examples of suitable abrasives include silicas and aluminas, and mixtures thereof. Preferably, the oral composition of the present invention includes silica. An example of a commercially available silica is Zenodent 113. Although the amount of the abrasive is suitably adjusted according to the material to be used, the oral composition of the present invention may include the abrasive in an amount of 0.1 to 30 mass % based on the composition. Preferably, the amount of the abrasive is 1 mass % to 15 mass % based on the composition.

The oral compositions of the present invention may include a wetting agent. Any wetting agent that has been conventionally used for an oral composition may be employed as the wetting agent. Examples of suitable wetting agents include polyglycerins such as glycerol and diglycerin, propylene glycol, dipropylene glycol, sorbitol, xylitol, mannitol, ethylene glycol, diethylene glycol, polyethylene glycol, and monomethyl ether. Two or more may be used in combination. Preferably, the oral composition of the present invention includes at least one of glycerol, propylene glycol or sorbitol. If propylene glycol is used, it can be mixed with paraben (e.g., 2% propylene glycol liquid with 1% paraben). Although the amount of the wetting agent is suitably adjusted according to the material to be used, the oral composition of the present invention may include the wetting agent in an amount of 0 mass % to 40 mass % based on the composition. Preferably, the amount of the wetting agent is 15 mass % to 30 mass % based on the composition.

The oral compositions of the present invention may include a surfactant. Any surfactant that has been conventionally used for an oral composition may be employed as the surfactant. The surfactant may be an anionic surfactant, a cationic surfactant, an amphoteric surfactant, a nonionic surfactant or mixtures thereof. Examples of suitable anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Preferably, the oral composition of the present invention includes sodium lauroyl sarcosinate. An example of a commercially available sodium lauroyl sarcosinate is Sarcosinate LN-30. Examples of suitable cationic surfactants include derivatives of aliphatic quaternary ammonium compounds having one long alkyl chain containing from 8 to 18 carbon atoms such as lauryl trimethylammonium chloride; cetyl pyridinium chloride; cetyl trimethylammonium bromide; diisobutylphenoxyethyldimethylbenzylammonium chloride; cetyl pyridinium fluoride; etc. Some of these cationic surfactants are also useful as anti-microbial agents. Examples of suitable amphoteric surfactants include cocoamidoethyl betaine, cocoamidopropyl betaine, lauramidopropyl betaine and the like. Examples of suitable nonionic surfactants include poloxamers, polyethylene oxide condensates of alkyl phenols, long chain tertiary amine oxides, long chain tertiary phosphine oxides, long chain dialkylsulfoxides and mixtures of such materials. Two or more may be used in combination. Although the amount of the surfactant is suitably adjusted according to the material to be used, the oral composition of the present invention may include the surfactant in an amount of 0 mass % to 40 mass % based on the composition. Preferably, the amount of the surfactant is 0 mass % to 10 mass % based on the composition, and more preferably is 0 mass % to 3 mass % based on the composition.

The oral composition of the present invention may include a coloring agent. Any coloring agent that has been conventionally used for an oral composition may be employed as the coloring agent. The coloring agent can be a water-soluble coloring agent. Examples of suitable coloring agents are titanium dioxide, and zinc oxide. Titanium dioxide is a white powder which adds opacity to the oral composition of the present invention. Preferably, the oral composition of the present invention includes titanium dioxide. Although the amount of coloring agent used is suitably adjusted according to the material to be used, the oral composition of the present invention may include the coloring agent in an amount of 0 mass % to 5 mass % based on the composition. Preferably, the amount of coloring agent is 0.5 mass % to 2 mass % based on the composition.

The oral composition of the present invention may include a sweetener or flavor. Any sweetener or flavor that has been conventionally used for an oral composition may be employed as the sweetener or flavor. Examples of suitable sweeteners include sucrose, sucralose, lactose, maltose, sorbitol, xylitol, sodium cyclamate, perillartine, AMP (aspartyl phenyl alanine, methyl ester), sodium saccharine, and the like. Preferably, the oral composition of the present invention includes saccharine, sorbitol or xylitol. In a preferred embodiment the oral composition of the present invention includes sodium saccharin. Examples of suitable flavors are flavoring oils, e.g. oil of spearmint, peppermint, wintergreen, sassafras, clove, sage, eucalyptus, marjoram, cinnamon, lemon, and orange, and methyl salicylate. Preferably, the oral composition of the present invention includes methyl salicylate. Although the amount of sweetener or flavor used is suitably adjusted according to the material to be used, the oral composition of the present invention may include the sweetener or flavor in an amount of 0 mass % to 10 mass % based on the composition. Preferably, the amount of sweetener or flavor is 0.5 mass % to 5 mass % based on the composition. In an embodiment, sorbitol can be used as a wetting agent and xylitol can be used as a sweetener or flavor.

Another aspect of the present invention is a method for the treatment of diseases caused by biofilms on teeth including administering the oral composition of the present invention to the mouth. In an embodiment, the oral composition is administered to the mouth of a mammal in need thereof. In a preferred embodiment, the oral composition is applied to teeth by, for example, brushing. The oral composition of the present invention is in the form of a solution, paste, gel or cream.

Another aspect of the present invention is a method for producing the oral composition. In an embodiment, the stannous ion source, CPP-ACP, and at least citric acid or citric acid salt is dissolved in water to obtain the oral composition. In another embodiment, the stannous ion source, CPP-ACP, and at least citric acid or citric acid salt is dissolved in water to obtain a first solution. If used, a sweetener or flavor can also be dissolved in the water to obtain the first solution. Additionally, if used, a wetting agent can also be dissolved in the water to obtain the first solution. If used, an inorganic thickener can be dispersed in the first solution. Separately, wetting agents, thickeners, and abrasives are dispersed in a separate container and the mixture is added to the first solution to obtain a dispersion. The dispersion is kneaded, and, if used, surfactants and flavors can be added to the kneaded dispersion, and kneading is performed to obtain the oral composition.

Examples

The present invention will now be further described with reference to the following non-limiting examples.

<Composition in Detail>

In Examples 1-6, oral compositions were prepared as set forth in Table 1. The Examples were prepared by dissolving sodium saccharin, xylitol, citric acid, trisodium citrate, stannous fluoride, sorbital, and CPP-ACP in purified water to obtain a first solution. Fumed silica was dispersed in the first solution. Separately, glycerol, propylene glycol, paraben, sodium carboxymethyl cellulose, titanium oxide, and abrasive silica were dispersed in a separate container, and the mixture was added to the first solution in which the fumed silica was dispersed to obtain a dispersion. The dispersion was kneaded, and methyl salicylate, sodium lauroyl sarcosinate and a flavor were added to the kneaded dispersion, and kneading was performed to obtain the oral composition.

The concentrations of CPP-ACP in Examples 1 to 3 were varied, and thus the concentrations of $SnF_2$ therein were also slightly varied. The concentrations of sodium citrate in Examples 4 to 6 were varied in addition to the concentrations of CPP-ACP. The compositions of Comparative Examples 1~4 did not include citric acid or sodium citrate. In addition, in the composition of Comparative Example 5, CPP-ACP was substituted with calcium chloride and potassium phosphate.

TABLE 1

| Example 1 | wt % | Example 2 | wt % | Example 3 | wt % |
| --- | --- | --- | --- | --- | --- |
| Purified Water | 42.2 | Purified Water | 47.1 | Purified Water | 49.6 |
| Sodium Saccharin | 0.1 | Sodium Saccharin | 0.1 | Sodium Saccharin | 0.1 |
| Xylitol | 1 | Xylitol | 1 | Xylitol | 1 |
| Citric acid | 0.2 | Citric acid | 0.1 | Citric acid | 0 |
| Trisodium citrate | 3.8 | Trisodium citrate | 3.9 | Trisodium citrate | 4 |
| Stannous fluoride | 0.5 | Stannous fluoride | 0.6 | Stannous fluoride | 0.6 |
| Sorbitol | 7 | Sorbitol | 7 | Sorbitol | 7 |
| CPP-ACP | 10 | CPP-ACP | 5 | CPP-ACP | 2.5 |
| Fumed silica | 2 | Fumed silica | 2 | Fumed silica | 2 |
| Glycerol | 18 | Glycerol | 18 | Glycerol | 18 |
| 2% Propylene glycol with 0.1% Paraben | 2.1 | 2% Propylene glycol with 0.1% Paraben | 2.1 | 2% Propylene glycol with 0.1% Paraben | 2.1 |
| Sodium carboxymethyl cellulose | 2.7 | Sodium carboxymethyl cellulose | 2.7 | Sodium carboxymethyl cellulose | 2.7 |
| Titanium Oxide | 1 | Titanium Oxide | 1 | Titanium Oxide | 1 |

TABLE 1-continued

| Example 4 | wt % | Example 5 | wt % | Example 6 | wt % |
|---|---|---|---|---|---|
| Purified Water | 40.1 | Purified Water | 43.2 | Purified Water | 49.3 |
| Sodium Saccharin | 0.1 | Sodium Saccharin | 0.1 | Sodium Saccharin | 0.1 |
| Xylitol | 1 | Xylitol | 1 | Xylitol | 1 |
| Citric acid | 0.3 | Citric acid | 0.2 | Citric acid | 0 |
| Trisodium citrate | 5.7 | Trisodium citrate | 7.8 | Trisodium citrate | 2 |
| Stannous fluoride | 0.6 | Stannous fluoride | 0.5 | Stannous fluoride | 0.4 |
| Sorbitol | 7 | Sorbitol | 7 | Sorbitol | 7 |
| CPP-ACP | 10 | CPP-ACP | 5 | CPP-ACP | 5 |
| Fumed silica | 2 | Fumed silica | 2 | Filmed silica | 2 |
| Glycerol | 18 | Glycerol | 18 | Glycerol | 18 |
| 2% Propylene glycol with 0.1% Paraben | 2.1 | 2% Propylene glycol with 0.1% Paraben | 2.1 | 2% Propyleneglycol with 0.1% Paraben | 2.1 |
| Sodium carboxymethyl cellulose | 2.7 | Sodium carboxymethyl cellulose | 2.7 | Sodium carboxymethyl cellulose | 2.7 |
| Titanium Oxide | 1 | Titanium Oxide | 1 | Titanium Oxide | 1 |
| Abrasive silica | 6.5 | Abrasive silica | 6.5 | Abrasive silica | 6.5 |
| Methyl Salicylate | 0.1 | Methyl Salicylate | 0.1 | Methyl Salicylate | 0.1 |
| sodium lauroyl sarcosinate (30% solution) | 1.3 | sodium lauroyl sarcosinate (30% solution) | 1.3 | sodium lauroyl sarcosinate (30% solution) | 1.3 |
| Flavor | 1.5 | Flavor | 1.5 | Flavor | 1.5 |
|  | 100.0 |  | 100.0 |  | 100.0 |

(Note: the continued table above also shows for Examples 1-3 the following footer rows: Abrasive silica 6.5; Methyl Salicylate 0.1; sodium lauroyl sarcosinate (30% solution) 1.3; Flavor 1.5; total 100.0.)

| Comparative Example 1 | wt % | Comparative Example 2 | wt % | Comparative Example 3 | wt % |
|---|---|---|---|---|---|
| Purified Water | 46.2 | Purified Water | 51.1 | Purified Water | 53.6 |
| Sodium Saccharin | 0.1 | Sodium Saccharin | 0.1 | Sodium Saccharin | 0.1 |
| Xylitol | 1 | Xylitol | 1 | Xylitol | 1 |
| Citric acid | 0 | Citric acid | 0 | Citric acid | 0 |
| Trisodium citrate | 0 | Trisodium citrate | 0 | Trisodium citrate | 0 |
| Stannous fluoride | 0.5 | Stannous fluoride | 0.6 | Stannous fluoride | 0.6 |
| Sorbitol | 7 | Sorbitol | 7 | Sorbitol | 7 |
| CPP-ACP | 10 | CPP-ACP | 5 | CPP-ACP | 2.5 |
| Fumed silica | 2 | Fumed silica | 2 | Fumed silica | 2 |
| Glycerol | 18 | Glycerol | 18 | Glycerol | 18 |
| 2% Propylene glycol with 0.1% Paraben | 2.1 | 2% Propylene glycol with 0.1% Paraben | 2.1 | 2% Propylene glycol with 0.1% Paraben | 2.1 |
| Sodium carboxymethyl cellulose | 2.7 | Sodium carboxymethyl cellulose | 2.7 | Sodium carboxymethyl cellulose | 2.7 |
| Titanium Oxide | 1 | Titanium Oxide | 1 | Titanium Oxide | 1 |
| Abrasive silica | 6.5 | Abrasive silica | 6.5 | Abrasive silica | 6.5 |
| Methyl Salicylate | 0.1 | Methyl Salicylate | 0.1 | Methyl Salicylate | 0.1 |
| sodium lauroyl sarcosinate (30% solution) | 1.3 | sodium lauroyl sarcosinate (30% solution) | 1.3 | sodium lauroyl sarcosinate (30% solution) | 1.3 |
| Flavor | 1.5 | Flavor | 1.5 | Flavor | 1.5 |
|  | 100.0 |  | 100.0 |  | 100.0 |

| Comparative Example 4 | wt % | Comparative Example 5 | wt % |
|---|---|---|---|
| Purified Water | 55.3 | Purified Water | 42.2 |
| Sodium Saccharin | 0.1 | Sodium Saccharin | 0.1 |
| Xylitol | 1 | Xylitol | 1 |
| Citric acid | 0 | Citric acid | 0.2 |
| Trisodium citrate | 0 | Trisodium citrate | 3.8 |
| Stannous fluoride | 0.4 | Stannous fluoride | 0.5 |
| Sorbitol | 7 | Sorbitol | 7 |
| CPP-ACP | 1 | CPP-ACP | 0 |
| Fumed silica | 2 | Calcium chloride dihydrate | 5.5 |
| Glycerol | 18 | Potassium phosphate tribasic | 4.5 |
| 2% Propylene glycol with 0.1% Paraben | 2.1 | Fumed silica | 2 |
| Sodium carboxymethyl cellulose | 2.7 | Glycerol | 18 |
| Titanium Oxide | 1 | 2% Propylene glycol with 0.1% Paraben | 2.1 |

TABLE 1-continued

| | | | |
|---|---|---|---|
| Abrasive silica | 6.5 | Sodium carboxymethyl cellulose | 2.7 |
| Methyl Salicylate | 0.1 | Titanium Oxide | 1 |
| sodium lauroyl sarcosinate (30% solution) | 1.3 | Abrasive silica | 6.5 |
| Flavor | 1.5 | Methyl Salicylate | 0.1 |
| | 100.0 | sodium lauroyl sarcosinate (30% solution) | 1.3 |
| | | Flavor | 1.5 |
| | | | 100.0 |

<Test Method>

The oral compositions of each example were stored at 60° C. for a week (assuming an acceleration test), and thereafter the soluble ion concentrations of F, Sn, Ca and Pi (phosphate ion; $PO_4^{3-}$), which were contained in a supernatant of a solution of the composition diluted by water ten times which was obtained by centrifugation, were measured, to calculate percentages to theoretical values thereof. The soluble ion concentration of F was measured by an electrode method, and the soluble ion concentrations of Sn, Ca and Pi were measured by colorimetry.

The measurement of the soluble ion concentrations in the oral compositions will be more specifically described using Example 1.

[Preparation] To 1.5 g of a paste, 13.5 g of ultra pure water was added and stirred using a stirrer for 30 minutes. The resultant was referred to as "diluted solution of the paste ten times".

[Measurement of F] To measure the electrode potential by a fluorine electrode method, 1.5 g of the diluted solution of the paste ten times, 7.5 g of a total-ionic strength adjustment buffer, and 6 g of ultra pure water were mixed. Likewise, the electrode potential in the case of a fluoride ion standard solution of a known concentration was measured, to make standard curves. The concentration of fluoride ions in the sample was calculated from the standard curves.

From 12.10 ppm, which is the calculation result, the concentration of soluble F ions contained in the paste was calculated as 1,210 ppm, which is 100 times as high as the calculation result. The amount of $SnF_2$ incorporated in Example 1 was 0.5 wt % (5,000 ppm). From the fact that the molecular weight of $SnF_2$ is 156.71 and the atomic weight of F is 19.00, the theoretical value of the concentration of soluble F ions was calculated as 1,212 ppm. Thus, the concentration of soluble F ions in Example 1 was calculated as 1,210/1,212×100=99.8 (100%) to the theoretical value.

[Measurement of Sn] The diluted solution of the paste ten times was diluted by 1 M of HCl 20 times. To 300 μL of the diluted solution by HCl, 390 μL of a liquid mixture of NaOH, lactic acid, and a sodium thiosulfate solution was added, and further 150 μL of a salicylideneamino-2-thiophenol (SATP) solution was added to be stirred, and thereafter left to stand still for 20 minutes. SATP reacts with a Sn ion, to turn yellow. To the resultant, 400 μL of xylene was added and strongly stirred, and thereafter a xylene layer was extracted to measure the absorbance at 415 nm. The same operation was carried out in the test system such that stannous ions of a known concentration were added, to calculate the concentration of soluble Sn ions in the diluted solution of the paste by the standard addition method.

In Example 1, the concentration of soluble Sn ions contained in the paste was calculated as 3,613 ppm. As noted above, the amount of $SnF_2$ incorporated in Example 1 was 0.5 wt % (5,000 ppm). From the fact that the molecular weight of $SnF_2$ is 156.71 and the atomic weight of Sn is 118.71, the theoretical value of the Sn concentration was calculated as 3,788 ppm. Thus, the concentration of soluble Sn ions in Provisional Example 1 was calculated as 3,613/3,788×100=95.41 (95%) to the theoretical value.

[Measurement of Ca] The diluted solution of the paste ten times was diluted by ultra pure water 20 times, and thereafter further diluted by 1 M of HCl twice. A kit for measuring Ca concentration, "QuantiChrom™ Calcium Assay Kit" was used to calculate the concentration of soluble Ca ions in the resultant diluted solution. By this measurement kit, blue coloration (612 nm) of phenolsulfonphthalein, which is specific to free calcium, was measured, and the concentration in the sample was calculated from the standard curves, to calculate the concentration of soluble Ca ions in the diluted solution.

In Example 1, the concentration of soluble Ca ions contained in the paste was calculated as 14,862 ppm. The amount of CPP-ACP incorporated in Example 1 was 10 wt % (equivalent to 15,000 ppm in terms of Ca). Thus, the concentration of soluble Ca ions in Example 1 was calculated as 14,862/15,000×100=99.1 (99%) to the theoretical value.

[Measurement of Pi] The diluted solution of the paste ten times was diluted by ultra pure water 10,000 times. A kit for measuring Pi concentration, "QuantiChrom™ Phosphate Assay Kit" was used to calculate the concentration of soluble Pi ions in the resultant diluted solution. By this measurement kit, color transition (620 nm) by formation of a complex of inorganic phosphate (Pi), malachite green, and molybdic acid was measured, to calculate the concentration in the sample from the standard curves.

In Example 1, the concentration of soluble Pi ions contained in the paste was calculated as 17,942 ppm. The amount of CPP-ACP incorporated in Example 1 was 10 wt % (equivalent to 18,000 ppm in terms of Pi). Thus, the concentration of soluble Pi ions in Provisional Example 1 was calculated as 17,942/18,000×100=99.7 (100%) to the theoretical value.

The soluble ion concentrations in the oral compositions of Examples 2-6 and Comparative Examples 1-5 were measured in the same manner as Example 1.

<Results>

The measurements of the soluble ion concentrations of Examples 1-6 and Comparative Example 1-5 are set forth in Table 2.

TABLE 2

| | Soluble ion concentration to the theoretical value (%) | | | |
|---|---|---|---|---|
| | F | Sn | Ca | Pi |
| Example 1 | 100 | 95 | 99 | 100 |
| Example 2 | 100 | 100 | 100 | 100 |

TABLE 2-continued

| | Soluble ion concentration to the theoretical value (%) | | | |
|---|---|---|---|---|
| | F | Sn | Ca | Pi |
| Example 3 | 93 | 72 | 73 | 89 |
| Example 4 | 96 | 100 | 100 | 99 |
| Example 5 | 100 | 81 | 92 | 91 |
| Example 6 | 100 | 94 | 97 | 98 |
| Comparative Example 1 | 83 | 39 | 82 | 85 |
| Comparative Example 2 | 79 | 45 | 82 | 86 |
| Comparative Example 3 | 38 | 16 | 49 | 51 |
| Comparative Example 4 | 3 | 3 | 35 | 48 |
| Comparative Example 5 | 71 | 42 | 82 | 65 |

<Evaluation>

The oral composition where the ion concentration of at least stannous ions and fluorine ions, after the composition was stored at 60° C. for a week, were at least 70% to the theoretical value was determined to have good stability. In addition, the oral compositions where the ion concentration of stannous ions, fluorine ions, and at least Pi ions or Ca ions, after the composition was stored at 60° C. for a week, were at least 70% to the theoretical value were determined to have even better stability. Further, the oral compositions where the ion concentration of stannous ions, fluorine ions, Pi ions and Ca ions, after the composition was stored at 60° C. for a week, were at least 70% to the theoretical value were determined to have excellent stability.

Specifically, as shown by Examples 1-6, even after long-term storage, the stannous ion concentration was kept high in the oral composition containing water, stannous fluoride, casein phosphopeptide-amorphous calcium phosphate, and at least citric acid or a citric acid salt. In contrast, the compositions of Comparative Examples 1-4 did not include citric acid or sodium citrate, and the concentration of stannous ions was lower that 70% to the theoretical value. In some of the compositions of the Comparative Examples, the concentration of stannous ions was significantly lower than 70% to the theoretical value. In addition, as can be seen from Comparative Example 5, when CPP-ACP was substituted with calcium chloride and potassium phosphate, the concentration of stannous ions was lower than 70% to the theoretical value.

While the subject matter disclosed herein has been described in connection with what is presently considered to be practical example embodiments, it is to be understood that the present disclosure is not limited to the disclosed embodiments, and covers various modifications and equivalent arrangements included within the spirit and scope of the present invention.

The invention claimed is:

1. An oral composition, the composition comprising:
   water,
   a stannous ion source,
   a fluoride ion source,
   casein phosphopeptide-amorphous calcium phosphate, and
   at least one of citric acid or citric acid salt,
   wherein a content of the casein phosphopeptide-amorphous calcium phosphate is 2.5 to 10 mass % based on the composition.

2. The oral composition according to claim 1, wherein the stannous ion source is stannous fluoride.

3. The oral composition according to claim 1, wherein the stannous ion source and the fluoride ion source is stannous fluoride.

4. The oral composition according to claim 1, wherein a content of the at least one of citric acid or citric acid salt is 2 to 8 mass % based on the composition.

5. The oral composition according to claim 2, wherein a content of the stannous fluoride is 0.4 to 0.6 mass % based on the composition.

6. The oral composition according to claim 1, wherein a content of the water is at least 30 mass % based on the composition.

7. The oral composition according to claim 1, wherein a content of the fluoride ion source is 0.4 to 0.5 mass % based on the composition.

* * * * *